United States Patent
Maleika et al.

(10) Patent No.: US 10,252,988 B2
(45) Date of Patent: *Apr. 9, 2019

(54) COMPOSITION FOR PRODUCING TRANSPARENT POLYTHIOURETHANE BODIES

(71) Applicant: Covestro Deutschland AG, Leverkusen (DE)

(72) Inventors: Robert Maleika, Düsseldorf (DE); Fredie Langenstueck, Leverkusen (DE); Christoph Eggert, Köln (DE); Irene C. Latorre Martinez, Leverkusen (DE); Josef Sanders, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/303,066

(22) PCT Filed: Apr. 13, 2015

(86) PCT No.: PCT/EP2015/057957
§ 371 (c)(1),
(2) Date: Oct. 10, 2016

(87) PCT Pub. No.: WO2015/155366
PCT Pub. Date: Oct. 15, 2015

(65) Prior Publication Data
US 2017/0121449 A1 May 4, 2017

(30) Foreign Application Priority Data
Apr. 11, 2014 (EP) .................................. 14164345

(51) Int. Cl.
| | | |
|---|---|---|
| *C07C 263/10* | (2006.01) | |
| *C08G 18/24* | (2006.01) | |
| *C08G 18/38* | (2006.01) | |
| *C08G 18/71* | (2006.01) | |
| *C08G 18/75* | (2006.01) | |
| *C08G 18/76* | (2006.01) | |
| *C08L 75/04* | (2006.01) | |
| *C08K 5/521* | (2006.01) | |
| *G02B 1/04* | (2006.01) | |

(52) U.S. Cl.
CPC .......... *C07C 263/10* (2013.01); *C08G 18/242* (2013.01); *C08G 18/3865* (2013.01); *C08G 18/3868* (2013.01); *C08G 18/3876* (2013.01); *C08G 18/714* (2013.01); *C08G 18/758* (2013.01); *C08G 18/7642* (2013.01); *C08K 5/521* (2013.01); *C08L 75/04* (2013.01); *G02B 1/041* (2013.01); *C08G 2125/00* (2013.01)

(58) Field of Classification Search
CPC ............ C08G 18/7642; C08G 18/3876; C08G 2125/00; C08G 18/758; C08G 18/242; C08G 18/3868; C08G 18/3865; C08G 18/714; C08K 5/521; G02B 1/041; C07C 263/10; C08L 75/04

See application file for complete search history.

(56) References Cited

U.S. PATENT DOCUMENTS

| | | | |
|---|---|---|---|
| 3,386,942 A * | 6/1968 | Bell ....................... | C08G 18/10 524/130 |
| 4,218,543 A | 8/1980 | Weber et al. | |
| 4,365,051 A * | 12/1982 | Chung ................... | C08G 18/10 528/64 |
| 4,680,369 A | 7/1987 | Kajimoto et al. | |

(Continued)

FOREIGN PATENT DOCUMENTS

| | | |
|---|---|---|
| DE | 1670666 A1 | 7/1971 |
| DE | 2622951 A1 | 11/1977 |

(Continued)

OTHER PUBLICATIONS

International Search Report for PCT/EP2015/057957 dated Jul. 10, 2015.

(Continued)

*Primary Examiner* — Patrick D Niland

(74) *Attorney, Agent, or Firm* — Drinker Biddle & Reath LLP

(57) ABSTRACT

The invention relates to a composition for producing transparent polythiourethane bodies containing or consisting of A) a polyisocyanate component containing at least one polyisocyanate with a functionality of isocyanate groups of at least 2 per molecule, B) a thiol component containing at least one polythiol with a functionality of thiol groups of at least two per molecule, in addition to optionally C) auxiliary agents and additives, the ratio of isocyanate groups to groups reactive in relation to isocyanates being 0.5:1 to 2.0:1. The composition is characterized in that the polyisocyanate of the polyisocyanate component A) is produced by a gasphase phosgenation of aliphatic, cycloaliphatic, aromatic or araliphatic polyamines. The invention also relates to a method for producing transparent polythiourethane bodies by the conversion of a composition of this type, to polythiourethane bodies produced in this manner and to the use of polyisocyanates, produced by a gas-phase phosgenation of aliphatic, cycloaliphatic, aromatic or araliphatic polyamines, for producing transparent polythiourethane bodies.

13 Claims, 1 Drawing Sheet

(56) References Cited

U.S. PATENT DOCUMENTS

| | | | |
|---|---|---|---|
| 4,689,387 A | 8/1987 | Kajimoto et al. | |
| 4,774,264 A | 9/1988 | Weber et al. | |
| 5,126,170 A | 6/1992 | Zwiener et al. | |
| 5,310,847 A | 5/1994 | Yean et al. | |
| 5,808,138 A * | 9/1998 | Laqua | C07C 263/18 560/331 |
| 5,914,383 A | 6/1999 | Richter et al. | |
| 6,730,768 B2 | 5/2004 | Heidbreder et al. | |
| 8,044,165 B2 | 10/2011 | Kawaguchi et al. | |
| 8,692,016 B2 | 4/2014 | Sanders et al. | |
| 2006/0155093 A1 | 7/2006 | Kitahara | |
| 2017/0029552 A1* | 2/2017 | Maleika | G02B 1/041 |
| 2017/0210702 A1* | 7/2017 | Halpaap | C07C 263/10 |

FOREIGN PATENT DOCUMENTS

| | | |
|---|---|---|
| DE | 2948419 A1 | 8/1981 |
| DE | 19701835 A1 | 7/1998 |
| EP | 0081701 A1 | 6/1983 |
| EP | 0081713 A2 | 6/1983 |
| EP | 0197543 A2 | 10/1986 |
| EP | 0235743 A1 | 9/1987 |
| EP | 0268896 A2 | 6/1988 |
| EP | 0271839 A2 | 6/1988 |
| EP | 0403921 A2 | 12/1990 |
| EP | 0408459 A1 | 1/1991 |
| EP | 0506315 A2 | 9/1992 |
| EP | 0586091 A2 | 3/1994 |
| EP | 0659792 A2 | 6/1995 |
| EP | 0689556 A1 | 1/1996 |
| EP | 0751161 A2 | 1/1997 |
| EP | 0798299 A1 | 10/1997 |
| EP | 0803743 A2 | 10/1997 |
| EP | 0937110 A1 | 8/1999 |
| EP | 0978523 A1 | 2/2000 |
| EP | 1437371 A1 | 7/2004 |
| EP | 1443067 A1 | 8/2004 |
| EP | 1640394 A1 | 3/2006 |
| EP | 1754698 A2 | 2/2007 |
| EP | 1908749 A1 | 4/2008 |
| EP | 1928928 A1 | 6/2008 |
| EP | 1988110 A1 | 11/2008 |
| GB | 1034152 A | 6/1966 |
| GB | 1145952 A | 3/1969 |
| JP | H05286978 A | 11/1993 |
| JP | H07118263 A | 5/1995 |
| JP | 2005161691 A | 6/2005 |
| JP | 2005162271 A | 6/2005 |
| WO | WO-9421702 A1 | 9/1994 |
| WO | WO-9821255 A1 | 5/1998 |
| WO | WO-2007039362 A1 | 4/2007 |
| WO | WO-2013079517 A1 | 6/2013 |

OTHER PUBLICATIONS

International Search Report for PCT/EP2015/057960 dated Jul. 23, 2015.

* cited by examiner

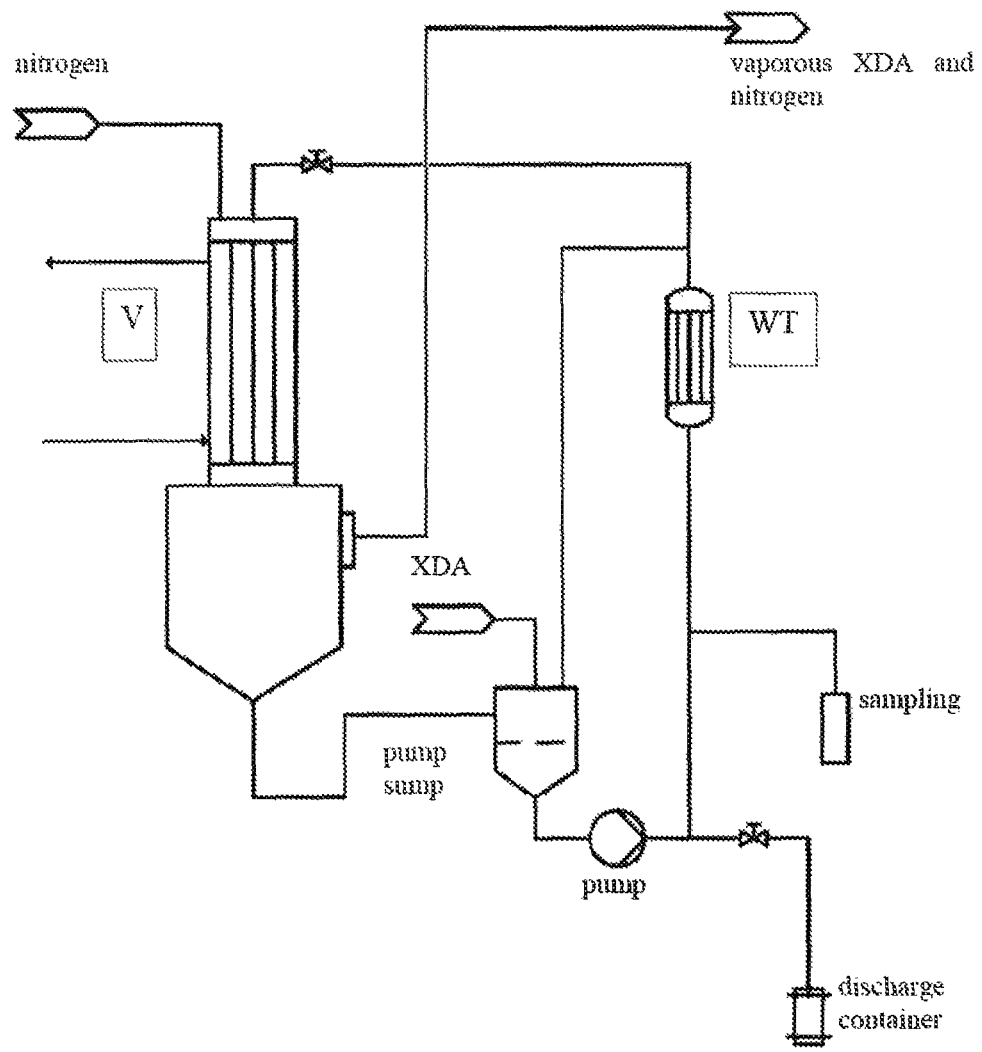

COMPOSITION FOR PRODUCING TRANSPARENT POLYTHIOURETHANE BODIES

CROSS-REFERENCE TO RELATED APPLICATIONS

This application is a national stage application (under 35 U.S.C. § 371) of PCT/EP2015/057957, filed Apr. 13, 2015, which claims benefit of European Application No. 14164345.2, filed Apr. 11, 2014, both of which are incorporated herein by reference in their entirety.

The present invention relates to compositions for producing transparent polythiourethane articles containing or consisting of
A) a polyisocyanate component containing at least one polyisocyanate having a functionality of isocyanate groups of at least 2 per molecule,
B) a thiol component containing at least one polythiol having a functionality of thiol groups of at least 2 per molecule
and optionally
C) auxiliary and additive agents,
wherein the ratio of isocyanate groups to isocyanate-reactive groups is 0.5:1 to 2.0:1. The invention further relates to a process for producing transparent polythiourethane articles by reaction of such a composition and to the thus manufactured polythiourethane articles and also to the use of polyisocyanates which are produced by gas-phase phosgenation of aliphatic, cycloaliphatic, aromatic or araliphatic polyamines for producing transparent polythiourethane articles.

BACKGROUND OF THE INVENTION

For various applications, for example as a lightweight substitute for mineral glass for producing panes for automobile and aircraft construction or as embedding compositions for optical, electronic or optoelectronic components, there is increasing interest on the market today in transparent, lightfast polyurethane compositions.

Particularly for high-quality optical applications, for example for lenses or spectacle glasses, there is generally a desire for plastics materials exhibiting high refraction coupled with low dispersion (high Abbe number).

The production of transparent polyurethane masses having a high refractive index has been described many times already. Araliphatic diisocyanates, i.e. diisocyanates whose isocyanate groups are bonded via aliphatic radicals to an aromatic system, are often used as polyisocyanate components. Owing to their aromatic structures, araliphatic diisocyanates afford polyurethanes having an increased refractive index while at the same time the aliphatic isocyanate groups guarantee the lightfastness and low yellowing tendency required for high-quality applications.

U.S. Pat. No. 4,680,369 and U.S. Pat. No. 4,689,387 describe polyurethanes/polythiourethanes suitable as lens materials for example, the production of which involves combining special sulfur-containing polyols or mercapto-functional aliphatic compounds with monomeric araliphatic diisocyanates, for example 1,3-bis(isocyanatomethyl)benzene (m-xylylene diisocyanate, m-XDI), 1,4-bis(isocyanatomethyl)benzene (p-xylylene diisocyanate, p-XDI), 1,3-bis(2-isocyanatopropan-2-yl)benzene (m-tetramethylxylylene diisocyanate, m-TMXDI) or 1,3-bis(isocyanatomethyl)-2,4,5,6-tetrachlorobenzene, in order to achieve particularly high refractive indices.

Monomeric araliphatic diisocyanates such as m- and p-XDI or m-TMXDI are also mentioned in numerous further publications, for example EP-A 0 235 743, EP-A 0 268 896, EP-A 0 271 839, EP-A 0 408 459, EP-A 0 506 315, EP-A 0 586 091 and EP-A 0 803 743, as the preferred polyisocyanate component for producing high refractivity lens materials. They serve as crosslinker components for polyols and/or polythiols and, depending on the coreactant, afford transparent plastics having high refractive indices in the range from 1.56 to 1.67 and comparatively high Abbe numbers up to 45.

A substantial disadvantage of the mentioned processes for producing high refractivity polyurethanes/polythiourethanes for optical applications is that some of the manufactured lenses do not always meet the desired standards in terms of their transparency and freedom from cloudiness. This applies especially to application in lenses and the like.

In order to satisfy the high requirements of optical applications, complex production processes for the raw materials are currently prior art. Thus, EP-A 1 908 749 describes the production of XDI, where initially the hydrochloride of the XDA is produced and this is then phosgenated under elevated pressure in order to obtain correspondingly pure grades. A direct phosgenation of the XDA would be desirable.

BRIEF SUMMARY OF THE INVENTION

The present invention accordingly has for its object to specify a composition for producing transparent polythiourethane articles which makes it possible to manufacture such articles with improved optical properties, in particular improved transparency and freedom from cloudiness.

This object is achieved in a composition of the type mentioned at the outset when the polyisocyanate of the polyisocyanate component A) is produced by gas-phase phosgenation of aliphatic, cycloaliphatic, aromatic or araliphatic polyamines.

The present invention accordingly provides a composition for producing transparent polythiourethane articles containing or consisting of
A) a polyisocyanate component containing at least one polyisocyanate having a functionality of isocyanate groups of at least 2 per molecule,
B) a thiol component containing or consisting of at least one polythiol having a functionality of thiol groups of at least 2 per molecule
and optionally
C) auxiliary and additive agents,
wherein the ratio of isocyanate groups to isocyanate-reactive groups is 0.5:1 to 2.0:1,
wherein the composition is characterized in that
the polyisocyanate of the polyisocyanate component A) is produced by gas-phase phosgenation of aliphatic, cycloaliphatic, aromatic or araliphatic polyamines.

In the context of the present invention, the term "transparent" is to be understood as meaning that the transparent article has a transmittance of >85% for a thickness of 2 mm and standard light type D65 (defined in DIN 6173). However, this transmittance value can deviate from the aforementioned value of >85% in the case of optional co-use of UV stabilizers and dyes.

DETAILED DESCRIPTION OF THE INVENTION

The present invention is based inter alia on the finding that polyisocyanates manufactured via gas-phase phosgenation can comprise a certain proportion of nitriles which, in the further processing of the polyisocyanates to afford polythiourethanes, improve the transparency of the thus manufactured molded articles. Without wishing to be bound to a particular theory it is believed that the nitriles act as solubility promoters for dimers or trimers of the polyisocyanate that are being formed. Without the nitrile these could precipitate which could be a possible reason for the formation of cloudiness.

A further advantage is that the composition according to the invention is less sensitive to entrained water than prior art systems as are described in U.S. Pat. No. 8,044,165 B2 for example. Normally, the thiol component in particular must be dried to remove excess water which could otherwise impair the optical properties of manufactured optical components. By contrast this is not necessary for the present invention. Thus the water content of the thiol component in the compositions according to the invention may be >600 ppm, in particular >800 ppm or even more than 900 ppm.

The invention provides that the polyisocyanate component contains at least one polyisocyanate having at least two isocyanate groups per molecule, in particular from 2 to 6, preferably from 2 to 4, particularly preferably from 2 to 3. It is also possible to employ mixtures of polyisocyanates of different functionality and odd-numbered average functionalities may therefore arise. In the context of the present invention the term polyisocyanate is to be understood as meaning organic isocyanates having two or more free isocyanate groups. The polyisocyanate may be in monomeric form or else in oligomeric form. Modification reactions suitable therefor are for example the customary processes for catalytic oligomerization of isocyanates to form uretdione, isocyanurate, iminooxadiazinedione and/or oxadiazinetrione structures or for biuretization of diisocyanates such as are described by way of example in Laas et al., J. Prakt. Chem. 336, 1994, 185-200, in DE-A 1 670 666 and in EP-A 0 798 299 for example. Specific descriptions of such polyisocyanates based on araliphatic diisocyanates may also be found in EP-A 0 081 713, EP-A 0 197 543, GB-A 1 034 152 and JP-A 05286978 for example. The syllable "poly" accordingly relates essentially to the number of isocyanate groups per molecule and does not necessarily mean that the polyisocyanate must have an oligomeric, much less a polymeric, structure.

The present invention provides that the polyisocyanate of the polyisocyanate component A) has been produced by gas-phase phosgenation of aliphatic, cycloaliphatic, aromatic or araliphatic polyamines. Such a process for manufacturing the polyisocyanates to be employed in accordance with the invention is described in EP 1 754 698 B1. Also employable is a process for gas-phase phosgenation as is disclosed in WO 2013/079517 A1.

The gas phase phosgenation procedure is preferably conducted such that the relevant starting substances, i.e. the polyamines upon which the polyisocyanates to be produced are based, are evaporated, optionally with addition of stabilizers and/or an inert gas, this being done at a pressure of <1000 mbar if necessary. The polyamines evaporated in this way are passed through a circuit with an average residence time of 5 to 90 minutes and a temperature of 40° C. to 190° C. and reacted with phosgene in accordance with processes of gas-phase phosgenation known per se at a temperature of 10 to 100 K above the evaporation temperature of the amines at the prevailing pressure. The above process conditions apply in particular to the manufacture of 1,3-xylylenediisocyanate and 1,4-xylylenediisocyanate. In this way, comparatively large amounts of nitrile are formed which have an advantageous effect on further processing in a composition according to the invention, in particular in terms of the transparency of molded articles manufactured therefrom. Complex separation of the nitriles may be eschewed.

Suitable modification reactions for producing the polyisocyanate components A) are, if desired, urethanization and/or allophanatization of araliphatic diisocyanates after addition of a molar deficiency of hydroxyl-functional coreactants, in particular low molecular weight mono- or polyhydric alcohols in the molecular weight range 32 to 300 g/mol, for example methanol, ethanol, n-propanol, isopropanol, n-butanol, isobutanol, sec-butanol, the isomeric pentanols, hexanols, octanols and nonanols, n-decanol, n-dodecanol, n-tetradecanol, n-hexadecanol, n-octadecanol, cyclohexanol, the isomeric methylcyclohexanols, hydroxymethylcyclohexane, 3-methyl-3-hydroxymethyloxetane, 1,2-ethanediol, 1,2- and 1,3-propanediol, the isomeric butanediols, pentanediols, hexanediols, heptanediols and octanediols, 1,2- and 1,4-cyclohexanediol, 1,4-cyclohexanedimethanol, 4,4'-(1-methylethylidene)biscyclohexanol, diethylene glycol, dipropylene glycol, 1,2,3-propanetriol, 1,1,1-trimethylolethane, 1,2,6-hexanetriol, 1,1,1-trimethylolpropane, 2,2-bis(hydroxymethyl)-1,3-propanediol or 1,3,5-tris(2-hydroxyethyl)isocyanurate, or any desired mixtures of such alcohols. Preferred alcohols for producing urethane- and/or allophanate-modified polyisocyanate components A) are the mentioned monoalcohols and diols having 2 to 8 carbon atoms.

Specific descriptions of urethane- and/or allophanate-modified polyisocyanates based on araliphatic diisocyanates may be found in EP-A 1 437 371, EP-A 1 443 067, JP-A 200516161691, JP-A 2005162271 for example.

In a preferred configuration of the composition according to the invention, the polyisocyanate component contains at least 80 wt % based on the polyisocyanate component of polyisocyanate produced by gas-phase phosgenation, in particular at least 85 wt %, more preferably at least 90 wt %, particularly preferably at least 95 wt % or even at least 96 or at least 98 wt %.

According to the invention, at least one nitrile present as a byproduct in the polyisocyanate component present by gas-phase phosgenation forms a further constituent of the polyisocyanate component. In addition to the polyisocyanate manufactured by gas-phase phosgenation the polyisocyanate component may quite possibly also have had at least one further polyisocyanate, for example manufactured by a different production route, added to it, for example a polyisocyanate produced by liquid-phase phosgenation. Depending on the nitrile content of the polyisocyanate component the proportion of polyisocyanates produced by routes other than gas-phase phosgenation may be for example up to 19 wt % based on the polyisocyanate component A), or else up to 14 wt %, up to 9 wt %, up to 4 wt/o or up to 3 wt %.

In a preferred embodiment of the composition according to the invention the polyisocyanate component contains at least 0.005 wt % based on the polyisocyanate component A) of at least one nitrile, in particular at least 0.01 wt %, preferably 0.005 to 15 wt %, more preferably 0.01 to 5 wt %, particularly preferably 0.1 to 2 wt % or even 0.1 to 1 wt %. As already stated hereinabove the polyisocyanate components employed in accordance with the invention and manufactured by gas-phase phosgenation may already contain a certain proportion of nitriles as a result of the production process which may be influenced inter alia by the nature of the polyamines employed in the reaction and moreover by the choice of the reaction conditions, in particular the pressure and the reaction temperature. This applies in particular for the polyisocyanates particularly preferred in the context of the present invention 1,3-bis(isocyanatomethyl)benzene (1,3-XDI) and 1,4-bis(isocyanatomethyl)benzene (1,4-XDI) which after the gas-phase phosgenation generally exhibit comparatively high contents of corresponding nitriles.

The abovementioned amounts of at least one nitrile in the polyisocyanate component may already be present in the polyisocyanate component as a result of the production procedure or else may be adjusted to the abovementioned amounts by deliberate additions of organic nitriles, in particular of aromatic nitriles. It is preferable when no additional nitrile over and above the content already resulting from the gas phase phosgenation production procedure is added. This applies with particular preference for a polyisocyanate component comprising 1,3-XDI and/or 1,4-XDI.

In the context of the present invention the content of nitriles is determined by derivatization with diethylamine and subsequent HPLC-MS by integration of the areas of the signals in the UV range. The HPLC-MS measurement may be performed with the following program for example:

Synapt G2-S HR-MS, ACQUITY UPLC (Waters) QS. No.: 02634
UV: PDA (Total Absorbance Chromatogram)
Column: Kinetex 100×2.1 mm_1.7 μm
Column temperature: 30° C.
The mobile phase consisted of:
Solvent: A) water+0.05% formic acid
B) acetonitrile+0.05% formic acid
Flow rate: 0.5 ml/min
Gradient: t0/5% B_t0.5/5% B_t6/100% B_t7/100% B_t7.1/5% B_t8/5% B In the context of the abovementioned embodiment it is particularly preferable when the nitrile is derived from the same polyamine as the polyisocyanate. This applies both for the nitriles present as a result of the production process and for any subsequently added nitriles. This is particularly advantageous since the identical basic chemical structure to that of the polyisocyanate manufactured during the gas-phase phosgenation ensures that a particularly good promotion effect is achieved by the nitrile.

It is particularly preferable here for the nitrile to contain at least one further functional group which is in particular a group that can be incorporated into the polythiourethane network to prevent later migration of the nitrile out of the molded article and may particularly preferably be an isocyanate group. This shall be elucidated hereinbelow with reference to the example 1,3-bis(isocyanatomethyl)benzene (1,3-XDI). This diisocyanate is manufactured by gas-phase phosgenation of 1,3-bis(aminomethyl)benzene. The particularly preferred isocyanatonitrile in this case is 3-(isocyantomethyl)benzonitrile.

The reaction of such an isocyanatonitrile with the thiol component can form nitrile-modified thiourethanes. This is shown using the example of 3-(isocyantomethyl)benzonitrile.

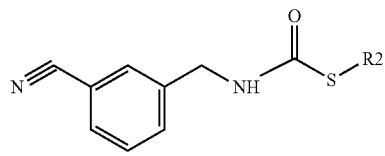

Here, R2 represents the radical of the polythiol employed. For 4-mercaptomethyl-1,8-dimercapto-3,6-dithiaoctane (DMPT) the radical R2 represents the following structural unit, wherein the left-hand bond line in the formula represents the bond to the sulfur atom in the above structure.

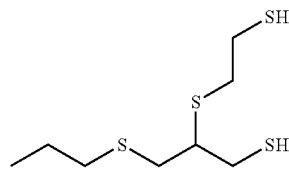

It is also possible for both thiol groups of the DMPT to react with one molecule of 3-(isocyantomethyl)benzonitrile respectively, thus forming the structure:

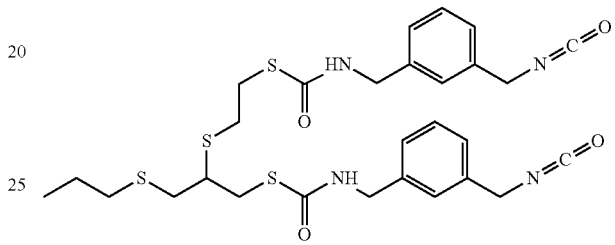

Analogous compounds may also be formed with optionally employed polyols. First, in general terms, the reaction product of 3-(isocyantomethyl)benzonitrile with a polyol where R1 represents the radical of the polyol employed:

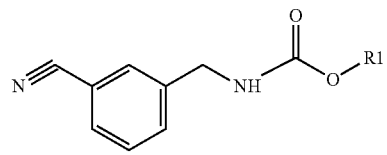

A nitrile-modified urethane is thus formed. When a diol is employed it is also possible for both OH groups to react with one molecule of 3-(isocyantomethyl)benzonitrile respectively, thus forming the structure:

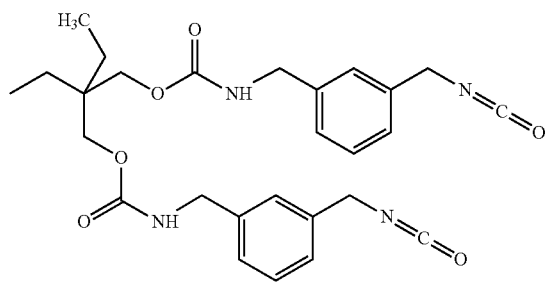 [SMILES: CCC(CC)(COC(=O)NCc1cccc(CN=C=O)c1)COC(=O)NCc1cccc(CN=C=O)c1]

Polyisocyanates that may be employed in the context of the present invention in principle include all polyisocyanates known per se. These are for example polyisocyanates in the molecular weight range 140 to 400 g/mol, for example 1,4-diisocyanatobutane, 1,5-diisocyanatopentane, 1,6-diisocyanatohexane (HDI), 1,5-diisocyanato-2,2-dimethylpentane, 2,2,4- or 2,4,4-trimethyl-1,6-diisocyanatohexane, 1,8-diisocyanatooctane, 1,9-diisocyanatononane, 1,10- diisocyanatodecane, 1,3- and 1,4-diisocyanatocyclohexane, 1,4-diisocyanato-3,3,5-trimethylcyclohexane, 1,3-diisocyanato-2-methylcyclohexane, 1,3-diisocyanato-4-methylcyclohexane, 1-isocyanato-3,3,5-trimethyl-5-isocyanatomethylcyclohexane (isophorone diisocyanate; IPDI), 1-isocyanato-1-methyl-4(3)-isocyanatomethylcyclohexane, 2,4'- and 4,4'-diisocyanatodicyclohexylmethane ($H_{12}$-MDI), 1,3- and 1,4-bis(isocyanatomethyl)cyclohexane, 4,4'-diisocyanato-3,3'-dimethyldicyclohexylmethane, 4,4'-diisocyanato-3,3',5,5'-tetramethyldicyclohexylmethane, 4,4'-diisocyanato-1,1'-10-bi(cyclohexyl), 2,5-bis(isocyanatomethyl)bicyclo[2.2.1]heptane, 2,6-bis(isocyanatomethyl)bicyclo[2.2.1]heptane, 4,4'-diisocyanato-3,3'-dimethyl-1,1'bi(cyclohexyl), 4,4'-diisocyanato-2,2',5,5'-tetramethyl-1,1'-bi(cyclohexyl), 1,8-diisocyanato-p-menthane, 1,3-diisocyanatoadamantane, 1,3-dimethyl-5,7-diisocyanatoadamantane, 1,3- and 1,4-bis(isocyanatomethyl)benzene, 1,3- and 1,4-bis(1-isocyanato-1-methylethyl)benzene (TMXDI), bis(4-(1-isocyanato-1-methylethyl)phenyl) carbonate, phenylene 1,3- and 1,4-diisocyanate, tolylene 2,4- and 2,6-diisocyanate and any desired mixtures of these isomers, diphenylmethane 2,4'- and/or 4,4'-diisocyanate and naphthylene 1,5-diisocyanate and any desired mixtures of such diisocyanates.

The polyisocyanates manufactured by gas-phase phosgenation are preferably selected from 1,3-bis(isocyanatomethyl)benzene (1,3-XDI), 1,4-bis(isocyanatomethyl)benzene (1,4-XDI), 2,5-bis(isocyanatomethyl)bicyclo[2.2.1]heptane, 2,6-bis(isocyanatomethyl)bicyclo[2.2.1]heptane, 1,3- and 1,4-bis(isocyanatomethyl)cyclohexane (H6-XDI), 2,4-diisocyanatotoluene, 2,6-diisocyanatotoluene, diphenylmethane 2,2'-diisocyanate, diphenylmethane 2,4'-diisocyanate, diphenylmethane 4,4'-diisocyanate (MDI) or mixtures thereof, in particular 1,3-bis(isocyanatomethyl)benzene (1,3-XDI) and/or 1,4-bis(isocyanatomethyl)benzene (1,4-XDI) or mixtures of 1,3-bis(isocyanatomethyl)benzene (1,3-XDI) and/or 1,4-bis(isocyanatomethyl)benzene (1,4-XDI) with others of the abovementioned isocyanates, but preferably 1,3-bis(isocyanatomethyl)benzene (1,3-XDI) and/or 1,4-bis(isocyanatomethyl)benzene (1,4-XDI). These poly- and diisocyanates are preferred because they make it possible to obtain lens materials having particularly good optical properties, such as a high refractive index and high transparency. These advantages are particularly pronounced for the diisocyanates mentioned as particularly preferable 1,3-bis(isocyanatomethyl)benzene (1,3-XDI) and 1,4-bis(isocyanatomethyl)benzene (1,4-XDI).

In a particularly preferred embodiment of the composition according to the invention the polyisocyanate is selected from 1,3-bis(isocyanatomethyl)benzene (1,3-XDI) and the nitrile from 3-(isocyanatomethyl)benzonitrile and/or that the polyisocyanate is selected from 1,4-bis(isocyanatomethyl)benzene (1,4-XDI) and the nitrile from 4-(isocyanatomethyl)benzonitrile.

The composition according to the invention further contains a thiol component B). Said component contains or consists of at least one polythiol having a functionality of thiol groups of at least two per molecule, in particular from 2 to 6, preferably from 2 to 4, particularly preferably from 2 to 3. It is also possible to employ mixtures of polythiols of different functionality and odd-numbered average functionalities may therefore arise. In the context of the present invention the term polythiol is to be understood as meaning organic thiols having two or more thiol groups. The syllable "poly" accordingly relates essentially to the number of thiol groups per molecule and, as stated above for the polyisocyanate compounds, does not necessarily mean that the polythiol must have an oligomeric, much less a polymeric, structure. Notwithstanding, the polythiols used according to the invention may quite possibly also have a polyether basic structure, a polythioether basic structure or a mixed basic structure composed of O-ether and S-ether units.

The polythiol may have an average molecular weight of 80 (methanedithiol) to about 12000 g/mol, preferably 250 to 8000 g/mol.

Suitable polythiols include for example methanedithiol, 1,2-ethanedithiol, 1,1-propanedithiol, 1,2-propanedithiol, 1,3-propanedithiol, 2,2-propanedithiol, 1,4-butanedithiol, 2,3-butanedithiol, 1,5-pentanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol and 2-methylcyclohexane-2,3-dithiol, polythiols containing thioether groups, for example 2,4-dimercaptomethyl-1,5-dimercapto-3-thiapentane, 4-mercaptomethyl-1,8-dimercapto-3,6-dithiaoctane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, 4,5-bis(mercaptoethylthio)-1,10-dimercapto-3,8-dithiadecane, tetrakis(mercaptomethyl)methane, 1,1,3,3-tetrakis(mercaptomethylthio)propane, 1,1,5,5-tetrakis(mercaptomethylthio)-3-thiapentane, 1,1,6,6-tetrakis(mercaptomethylthio)-3,4-dithiahexane, 2-mercaptoethylthio-1,3-dimercaptopropane, 2,3-bis(mercaptoethylthio)-1-mercaptopropane, 2,2-bis(mercaptomethyl)-1,3-dimercaptopropane, bis(mercaptomethyl) sulfide, bis(mercaptomethyl) disulfide, bis(mercaptoethyl) sulfide, bis(mercaptoethyl) disulfide, bis(mercaptopropyl) sulfide, bis(mercaptopropyl) disulfide, bis-(mercaptomethylthio)methane, tris(mercaptomethylthio)methane, bis(mercaptoethylthio)methane, tris(mercaptoethylthio)methane, 12-bis(mercaptopropylthio)methane, 1,2-bis(mercaptomethylthio)ethane, 1,2-bis(mercaptoethylthio)ethane, 2-(mercaptoethylthio)ethane, 1,3-bis(mercaptomethylthio)propane, 1,3-bis(mercaptopropylthio)propane, 1,2,3-tris(mercaptomethylthio)propane, 1,2,3-tris(mercaptoethylthio)propane, 1,2,3-tris(mercaptopropylthio)propane, tetrakis(mercaptomethylthio)methane, tetrakis(mercaptoethylthiomethyl)methane, tetrakis(mercaptopropylthiomethyl)methane, 2,5-dimercapto-1,4-dithiane, 2,5-bis(mercaptomethyl)-1,4-dithiane and oligomers thereof obtainable as described in JP-A 07118263, 1,5-bis(mercaptopropyl)-1,4-dithiane, 1,5-bis(2-mercaptoethylthiomethyl)-1,4-dithiane, 2-mercaptomethyl-6-mercapto-1,4-dithiacycloheptane, 2,4,6-trimercapto-1,3,5-trithiane, 2,4,6-trimercaptomethyl-1,3,5-trithiane and 2-(3-bis(mercaptomethyl)-2-thiapropyl)-1,3-dithiolane, polyester thiols, for example ethylene glycol bis(2-mercaptoacetate), ethylene glycol bis(3-mercaptopropionate), diethylene glycol 2-mercaptoacetate, diethylene glycol 3-mercaptopropionate, 2,3-dimercapto-1-propanol 3-mercaptopropionate, 3-mercapto-1,2-propanediol bis(2-mercaptoacetate), 3-mercapto-1,2-propanediol bis(3-mercaptopropionate), trimethylolpropane tris(2-mercaptoacetate), trimethylolpropane tris(3-mercaptopropionate), trimethylolethane tris(2-mercaptoacetate), trimethylolethane tris(3-mercaptopropionate), pentaerythritol tetrakis(2-mercaptoacetate), pentaerythritol tetrakis(3-mercaptopropionate), glycerol tris(2-mercaptoacetate), glycerol tris(3-mercaptopropionate), 1,4-cyclohexanediol bis(2-mercaptoacetate), 1,4-cyclohexanediol bis(3-mercaptopropionate), hydroxymethyl sulfide bis(2-mercaptoacetate), hydroxymethyl sulfide bis(3-mercaptopropionate), hydroxyethyl sulfide 2-mercaptoacetate, hydroxyethyl sulfide 3-mercaptopropionate, hydroxymethyl disulfide 2-mercaptoacetate, hydroxymethyl disulfide 3-mercaptopropionate, 2-mercaptoethyl ester thioglycolate and bis(2-mercaptoethyl ester) thiodipropionate and also aromatic thio compounds, for example 1,2-dimercaptobenzene, 1,3-dimercaptobenzene, 1,4-dimercaptobenzene, 1,2-bis(mercaptomethyl)benzene, 1,4-bis(mercaptomethyl)benzene, 1,2-bis(mercaptoethyl)benzene, 1,4-bis(mercaptoethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,3,5-tris(mercaptoethyl)benzene, 1,2,4-tris(mercaptoethyl)benzene, 2,5-toluenedithiol, 3,4-toluenedithiol, 1,4-naphthalenedithiol, 1,5-naphthalenedithiol, 2,6-naphthalenedithiol, 2,7-naphthalenedithiol, 1,2,3,4-tetramercaptobenzene, 1,2,3,5-tetramercaptobenzene, 1,2,4,5-tetramercaptobenzene, 1,2,3,4-tetrakis(mercaptomethyl)benzene, 1,2,3,5-tetrakis(mercaptomethyl)benzene, 1,2,4,5-tetrakis(mercaptomethyl)benzene, 1,2,3,4-tetrakis(mercaptoethyl)benzene, 1,2,3,5-tetrakis(mercaptoethyl)benzene, 1,2,4,5-tetrakis(mercaptoethyl)benzene, 2,2'-dimercaptobiphenyl and 4,4'-dimercaptobiphenyl.

It is preferable when the polythiol is selected from 4-mercaptomethyl-1,8-dimercapto-3,6-dithiaoctane, 2,5-bismercaptomethyl-1,4-dithiane, 1,1,3,3-tetrakis(mercaptomethylthio)propane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, trimethylolpropane tris(3-mercaptopropionate), trimethylolethane tris(2-mercaptoacetate), pentaerythritol tetrakis(2-mercaptoacetate) and/or pentaerythritol tetrakis(3-mercaptopropionate).

Aside from the thiol component B) the composition according to the invention may also contain other components typically reacted with polyisocyanates. These are in particular the customary polyetherpolyols, polyesterpolyols, polyetherpolyesterpolyols, polythioetherpolyols, polymer-modified polyetherpolyols, graft polyetherpolyols, in particular those based on styrene and/or acrylonitrile, polyetherpolyamines, hydroxyl-containing polyacetals and/or hydroxyl-containing aliphatic polycarbonates known from polyurethane chemistry which typically have a weight-average molecular weight of 106 to 12 000 g/mol, preferably 250 to 8000 g/mol. A broad overview of suitable coreactants B) may be found for example in N. Adam et al.: "Polyurethanes", Ullmann's Encyclopedia of Industrial Chemistry, Electronic Release, 7th ed., chap. 3.2-3.4, Wiley-VCH, Weinheim 2005.

In the context of the present invention the term polythiourethane is to be understood as meaning a polymer where more than half to all of the bonds between the polyisocyanate and the isocyanate-reactive component(s) are thiourethane groups. Thus, other bonds may be present in a proportion of less than half, for example urethane or urea bridges. In this case the composition according to the invention also contains other isocyanate-reactive component(s). These merely optional components are more particularly described hereinbelow.

Suitable polyetherpolyols, if used, are for example those of the type referred to in DE-A 2 622 951, column 6, line 65—column 7, line 47, or EP-A 0 978 523, page 4, line 45 to page 5, line 14, provided that they conform to the above indications relating to functionality and molecular weight. Particularly preferred polyetherpolyols B) are addition products of ethylene oxide and/or propylene oxide onto glycerol, trimethylolpropane, ethylenediamine and/or pentaerythritol.

Suitable polyesterpolyols, if used, are for example those of the type referred to in EP-A 0 978 523, page 5, lines 17 to 47, or EP-A 0 659 792, page 6, lines 8 to 19, provided that they conform to the above indications, preferably those having a hydroxyl number of 20 to 650 mg KOH/g.

Suitable polyacetalpolyols, if used, are for example the known reaction products of simple glycols, for example diethylene glycol, triethylene glycol, 4,4'-dioxyethoxydiphenyldimethylmethane (adduct of 2 mol of ethylene oxide onto bisphenol A) or hexanediol, with formaldehyde, or else polyacetals produced by polycondensation of cyclic acetals, for example trioxane.

Aminopolyethers or mixtures of aminopolyethers may likewise be suitable, i.e. polyethers having isocyanate-reactive groups which are composed of primary and/or secondary, aromatic or aliphatic amino groups to an extent of at least 50 equivalent %, preferably at least 80 equivalent %, and of primary and/or secondary, aliphatic hydroxyl groups as the remainder. Suitable aminopolyethers of this type are for example the compounds referred to in EP-A 0 081 701, column 4, line 26 to column 5, line 40. Likewise suitable as starting component E) are amino-functional polyethinirethanes or -ureas such as are producible for example by the process of DE-A 2 948 419 by hydrolysis of isocyanate-functional polyether prepolymers or else amino-containing polyesters of the abovementioned molecular weight range.

Further suitable isocyanate-reactive components are, for example, also those described in EP-A 0 689 556 and EP-A 0 937 110, for example special polyols obtainable by reaction of epoxidized fatty acid esters with aliphatic or aromatic polyols to bring about epoxide ring opening.

Hydroxyl-containing polybutadienes too may optionally be employed.

Sulfur-containing hydroxyl compounds are moreover also suitable as isocyanate-reactive components. Examples that may be mentioned here are mercaptoalcohols, for example 2-mercaptoethanol, 3-mercaptopropanol, 1,3-dimercapto-2-propanol, 2,3-dimercaptopropanol and dithioerythritol, thioether-containing alcohols, for example di(2-hydroxyethyl)sulfide, 1,2-bis(2-hydroxyethylmercapto)ethane, bis(2-hydroxyethyl)disulfide and 1,4-dithiane-2,5-diol, or sulfur-containing diols having a polyesterurethane-, polythioesterurethane-, polyesterthiourethane- or Polythioesterthiourethane structure of the type referred to in EP-A 1 640 394.

The compositions according to the invention may also contain as isocyanate-reactive compounds low molecular weight, hydroxyl- and/or amino-functional components, i.e. those in a molecular weight range from 60 to 500 g/mol, preferably from 62 to 400 g/mol.

These are for example simple mono- or polyhydric alcohols having 2 to 14, preferably 4 to 10 carbon atoms, for example 1,2-ethanediol, 1,2- and 1,3-propanediol, the isomeric butanediols, pentanediols, hexanediols, heptanediols and octanediols, 1,10-decanediol, 1,2- and 1,4-cyclohexanediol, 1,4-cyclohexanedimethanol, 4,4'-(1-methylethylidene)biscyclohexanol, 1,2,3-propanetriol, 1,1,1-trimethylolethane, 1,2,6-hexanetriol, 1,1,1-trimethylolpropane, 2,2-bis(hydroxymethyl)-1,3-propanediol, bis(2-hydroxyethyl)hydroquinone, 1,2,4- and 1,3,5-trihydroxycyclohexane or 1,3,5-tris(2-hydroxyethyl)isocyanurate.

Examples of suitable low molecular weight amino-functional compounds are aliphatic and cycloaliphatic amines and aminoalcohols having primary and/or secondary amino groups, for example cyclohexylamine, 2-methyl-1,5-pentanediamine, diethanolamine, monoethanolamine, propylamine, butylamine, dibutylamine, hexylamine, monoisopropanolamine, diisopropanolamine, ethylenediamine, 1,3-diaminopropane, 1,4-diaminobutane, isophoronediamine, diethylenetriamine, ethanolamine, aminoethylethanolamine, diaminocyclohexane, hexamethylenediamine, methyliminobispropylamine, iminobispropylamine, bis(aminopropyl)piperazine, aminoethylpiperazine, 1,2-diaminocyclohexane, triethylenetetramine, tetraethylenepentamine, 1,8-p-diaminomenthane, bis(4-aminocyclohexyl)methane, bis(4-amino-3-methylcyclohexyl)methane, bis(4-amino-3,5-dimethylcyclohexyl)methane, bis(4-amino-2,3,5-trimethylcyclohexyl)methane, 1,1-bis(4-aminocyclohexyl)propane, 2,2-bis(4-aminocyclohexyl)propane, 1,1-bis(4-aminocyclohexyl)ethane, 1,1-bis(4-aminocyclohexyl)butane, 2,2-bis(4-aminocyclohexyl)butane, 1,1-bis(4-amino-3-methylcyclohexyl)ethane, 2,2-bis(4-amino-3-methylcyclohexyl)propane, 1,1-bis(4-amino-3,5-dimethylcyclohexyl)ethane, 2,2-bis(4-amino-3,5-dimethylcyclohexyl)propane, 2,2-bis(4-amino-3,5-dimethylcyclohexyl)butane, 2,4-diaminodicyclohexylmethane, 4-aminocyclohexyl-4-amino-3-methylcyclohexylmethane, 4-amino-3,5-dimethylcyclohexyl-4-amino-3-methylcyclohexylmethane and 2-(4-aminocyclohexyl)-2-(4-amino-3-methylcyclohexyl)methane.

Examples of aromatic polyamines, in particular diamines, having molecular weights below 500 which are suitable isocyanate-reactive compounds B) are for example 1,2- and 1,4-diaminobenzene, 2,4- and 2,6-diaminotoluene, 2,4'- and/or 4,4'-diaminodiphenylmethane, 1,5-diaminonaphthalene, 4,4',4''-triaminotriphenylmethane, 4,4'-bis(methylamino)diphenylmethane or 1-methyl-2-methylamino-4-aminobenzene, 1-methyl-3,5-diethyl-2,4-diaminobenzene, 1-methyl-3,5-diethyl-2,6-diaminobenzene, 1,3,5-trimethyl-2,4-diaminobenzene, 1,3,5-triethyl-2,4-diaminobenzene, 3,5,3',5'-tetraethyl-4,4'-diaminodiphenylmethane, 3,5,3',5'-tetraisopropyl-4,4'-diaminodiphenylmethane, 3,5-diethyl-3',5'-diisopropyl-4,4'-diaminodiphenylmethane, 3,3'-diethyl-5,5'-diisopropyl-4,4'-diaminodiphenylmethane, 1-methyl-2,6-diamino-3-isopropylbenzene, liquid mixtures of polyphenylpolymethylenepolyamines, such as are obtainable in known fashion by condensation of aniline with formaldehyde, and any desired mixtures of such polyamines. In this connection particular mention may be made of mixtures of 1-methyl-3,5-diethyl-2,4-diaminobenzene with 1-methyl-3,5-diethyl-2,6-diaminobenzene in a weight ratio of 50:50 to 85:15, preferably of 65:35 to 80:20.

The use of low molecular weight amino-functional polyethers having molecular weights below 500 g/mol is likewise possible. These are for example those which have primary and/or secondary, aromatic or aliphatic amino groups, said amino groups optionally being bonded to the polyether chains via urethane or ester groups, and which are obtainable by known processes already described above in connection with production of the higher molecular weight aminopolyethers.

Sterically hindered aliphatic diamines having two secondary amino groups may optionally also be employed as isocyanate-reactive components, for example the reaction products of aliphatic and/or cycloaliphatic diamines with maleic or fumaric esters disclosed in EP-A 0 403 921 or the hydrogenation products of Schiff bases obtainable from aliphatic and/or cycloaliphatic diamines and ketones, for example diisopropyl ketone, described in DE-A 19 701 835 for example.

In addition to the mentioned starting components A) and B), auxiliary and additive agents (C), for example catalysts, surface-active agents, UV stabilizers, antioxidants, fragrances, mold release agents, fillers and/or pigments, may optionally be co-used.

For the purpose of reaction acceleration it is possible to employ, for example, customary catalysts known from polyurethane chemistry. By way of example mention may be made here of tertiary amines, for example triethylamine, tributylamine, dimethylbenzylamine, diethylbenzylamine, pyridine, methylpyridine, dicyclohexylmethylamine, dimethylcyclohexylamine, N,N,N',N'-tetramethyldiaminodiethyl ether, bis(dimethylaminopropyl)urea, N-methyl-/N-ethylmorpholine, N-cocomorpholine, Ncyclohexylmorpholine, N,N,N',N'-tetramethylethylenediamine, N,N,N',N'-tetramethyl-1,3-butanediamine, N,N,N', N'-tetramethyl-1,6-hexanediamine, pentamethyldiethylenetriamine, N-methylpiperidine, N-dimethylaminoethylpiperidine, N,N-dimethylpiperazine, N-methyl-N'-dimethylaminopiperazine, 1,8-diazabicyclo(5.4.0)undec-7-ene (DBU), 1,2-dimethylimidazole, 2-methylimidazole, N,N-dimethylimidazol-β-phenylethylamine, 1,4-diazabicyclo-(2,2,2)-octane, bis(N,N-dimethylaminoethyl)adipate; alkanolamine compounds, for example triethanolamine, triisopropanolamine, N-methyl- and N-ethyldiethanolamine, dimethylaminoethanol, 2-(N,N-dimethylaminoethoxy)ethanol, N,N',N''-tris(dialkylaminoalkyl)hexahydrotriazines, for example N,N', N''-tris(dimethylaminopropyl)-s-hexahydrotriazine and/or bis(dimethylaminoethyl) ether, metal salts, for example inorganic and/or organic compounds of iron, lead, bismuth, zinc and/or tin in customary oxidation states of the metal, for example iron(II) chloride, iron(III) chloride, bismuth(III) bismuth(III) 2-ethylhexanoate, bismuth(III) octoate, bismuth(III) neodecanoate, zinc chloride, zinc 2-ethylcaproate, tin(II) octoate, tin(II) ethylcaproate, tin(II) palmitate, dibutyltin(IV) dilaurate (DBTL), dibutyltin(IV) dichloride or lead octoate; amidines, for example 2,3-dimethyl-3,4,5,6-tetrahydropyrimidine; tetraalkylammonium hydroxides, for example tetramethylammonium hydroxide; alkali metal hydroxides, for example sodium hydroxide, and alkali metal alkoxides, for example sodium methoxide and potassium isopropoxide, and also alkali metal salts of long-chain fatty acids having 10 to 20 carbon atoms and optionally lateral OH groups.

Preferred catalysts C) for use are tertiary amines, bismuth and tin compounds of the type mentioned.

The catalysts mentioned by way of example may be used in the production of the lightfast polyurethane, polythiourethane and/or polyurea masses according to the invention individually or in the form of any desired mixtures with one another and are optionally employed in amounts of 0.001 to 5.0 wt %, preferably 0.002 to 2 wt %, calculated as the total amount of catalysts employed based on the total amount of the starting compounds employed.

The compositions according to the invention are preferably used to produce transparent, compact moldings having a high refractive index.

The articles obtained from the compositions according to the invention feature very good light resistance even as such, i.e. without addition of appropriate stabilizers. Nevertheless, known UV-protectants (light stabilizers) or antioxidants may be co-used as auxiliary and additive agents C).

Suitable UV stabilizers C) are for example piperidine derivatives, for example 4-benzoyloxy-2,2,6,6-tetramethylpiperidine, 4-benzoyloxy-1,2,2,6,6-pentamethylpiperidine, bis(2,2,6,6-tetramethyl-4-piperidyl) sebacate, bis(1,2,2,6,6- pentamethyl-4-piperidyl) sebacate, methyl (1,2,2,6,6-pentamethyl-4-piperidyl) sebacate, bis(2,2,6,6-tetramethyl-4-piperidyl) suberate or bis(2,2,6,6-tetramethyl-4-piperidyl) dodecanedioate, benzophenone derivatives, for example 2,4-dihydroxy-, 2-hydroxy-4-methoxy-, 2-hydroxy-4-octoxy-, 2-hydroxy-4-dodecyloxy- or 2,2'-dihydroxy-4-do-decyloxybenzophenone, benzotriazole derivatives, for example 2-(5-methyl-2-hydroxyphenyl)benzotriazole, 2-(5-tert-butyl-2-hydroxyphenyl)benzotriazole, 2-(5-tertoctyl-2-hydroxyphenyl)benzotriazole, 2-(5-dodecyl-2-hydroxyphenyl)benzotriazole, 2-(3,5-di-tert-butyl-2-hydroxyphenyl)-5-chlormrbenzotriazole, 2-(3,5-di-tert-amyl-2-hydroxyphenyl)benzotriazole, 2-(3,5-di-tert-butyl-2-hydroxyphenyl)benzotriazole, 2-(3-tert-butyl-5-methyl-2-hydroxyphenyl)-5-chlorobenzotriazole and esterification products of 2-(3-tert-butyl-5-propionato-2-hydroxyphenyl)benzotriazole with polyethylene glycol 300, oxalanilides, for example 2-ethyl-2'-ethoxy- or 4-methyl-4'-methoxyoxalanilide, salicylic esters, for example phenyl salicylate, 4-tert-butylphenyl salicylate and 4-tertoctylphenyl salicylate; cinnamic ester derivatives, for example methyl α-cyano-β-methyl-4-methoxycinnamate, butyl α-cyano-β-methyl-4-methoxycinnamate, ethyl α-cyano-β-phenylcinnamate and isooctyl α-cyano-β-phenylcinnamate, or malonic ester derivatives, for example dimethyl 4-methoxybenzylidenemalonate, diethyl 4-methoxybenzylidenemalonate, and dimethyl 4-butoxybenzylidenemalonate. These light stabilizers may be employed either individually or in any desired combinations with one another.

Suitable antioxidants C) are for example the known sterically hindered phenols, for example 2,6-di-tert-butyl-4-methylphenol (Ionol), pentaerythritol tetrakis(3-(3,5-di-tert-butyl-4-hydroxyphenyl)propionate), octadecyl-3-(3,5-di-tert-butyl-4-hydroxyphenyl)propionate, triethylene glycol bis(3-tert-butyl-4-hydroxy-5-methylphenyl)propionate, 2,2'-thiobis(4-methyl-6-tert-butylphenol), 2,2'-thiodiethyl-bis[3-(3,5-di-tert-butyl-4-hydroxyphenyl)propionate), which may be employed either individually or in any desired combinations with one another.

Finally, it is also possible to co-use the internal mold release agents, dyes, pigments, hydrolysis inhibitors, fungistatic and bacteriostatic substances known per se.

It is particularly preferable when the composition according to the invention contains as component C) at least one mold release agent selected from mono- and/or dialkyl phosphates and/or mono- and/or dialkoxyalkyl phosphates. As mono- and/or dialkyl phosphates, particularly mono- and/or dialkyl phosphates having 2 to 18 carbon atoms in the alkyl radical, preferably 8 to 12 carbon atoms, are. Particularly preferred mono/dialkoxyalkyl phosphates have 2 to 12 carbon atoms in the alkoxyalkyl radical and up to three ether groups per alkoxyalkyl radical, the abovementioned mono-/alkoxyalkyl phosphates having in particular 4 to 10 carbon atoms in the alkoxyalkyl radical. The preferred mono-/dialkyl phosphates and mono-/dialkoxyalkyl phosphates are particularly advantageous since in addition to their actual function as a mold release agent they also have a favorable effect on the reaction rate in the reaction of the polyisocyanate component with the thiol component in the respect that their addition reduces the reaction rate of the two components with one another. This ultimately results in molded articles of higher optical quality and in simpler handling of the composition after the mixing of the components.

Suitable mold release agents are for example methyl phosphate, dimethyl phosphate, methoxyethyl phosphate, methoxypropyl phosphate, di(methoxyethyl) phosphate, methoxyethyl ethoxyethyl phosphate, methoxyethyl propoxyethyl phosphate, di(methoxypropyl) phosphate, ethyl phosphate, diethyl phosphate, ethoxyethyl phosphate, di(ethoxyethyl) phosphate, ethoxypropyl phosphate, ethoxyethyl propoxyethyl phosphate, di(ethoxypropyl) phosphate, ethoxyethyl butoxyethyl phosphate, isopropyl phosphate, diisopropyl phosphate, propoxyethyl phosphate, di(propoxyethyl) phosphate, propoxypropyl phosphate, di(propoxylpropyl) phosphate, butyl phosphate, dibutyl phosphate, butoxyethyl phosphate, butoxypropyl phosphate, di(butoxyethyl) phosphate, pentoxyethyl phosphate, bis(2-ethylhexyl) phosphate, di(hexyloxyethyl) phosphate, octyl phosphate, dioctyl phosphate, decyl phosphate, isodecyl phosphate, diisodecyl phosphate, isodecyloxyethyl phosphate, di(decyloxyethyl) phosphate, dodecyl phosphate, didoceyl phosphate, tridecanol phosphate, bis(tridecanol) phosphate, stearyl phospate, distearyl phosphate and any desired mixtures of such compounds.

The compositions according to the invention advantageously contain 0.01 to 4 wt % of mono-/dialkylphosphates and/or mono-/dialkylalkoxyphosphates, preferably 0.02 to 2 wt %, based on the overall composition. The abovementioned usage amounts relate to the total content of these substances as mold release agents.

A particularly preferable composition according to the invention for producing transparent polythiourethane articles contains or consists of A) 35 to 65 wt % based on the composition, in particular 45 to 55 wt %, of a polyisocyanate component containing
at least 90 to 99.8 wt %, in particular 95 to 99.7 wt %, based on the polyisocyanate component of a polyisocyanate selected from 1,3-XDI and/or 1,4-XDI having a functionality of isocyanate groups of 2 per molecule and 0.05 to 2 wt %, in particular 0.1 to 1 wt %, based on the polyisocyanate component of 3-(isocyanatomethyl)benzonitrile and/or 4-(isocyanatomethyl)benzonitrile, B) 35 to 65 wt % based on the composition, in particular 45 to 55 wt %, of a thiol component containing at least one polythiol having a functionality of thiol groups of at least 2 per molecule, wherein the thiol component in particular consists of a polythiol having a functionality of thiol groups of 3 per molecule, namely DMPT (4-mercaptomethyl-1,8-dimercapto-3,6-dithiaoctane), and C) auxiliary and additive agents comprising 0.01 to 4 wt %, in particular 0.02 to 0.5 wt %, of a mold release agent selected from mono- and/or dialkyl phosphates having 2 to 18 carbon atoms in the alkyl radical and/or mono- and/or dialkoxyalkyl phosphates having 2 to 12 carbon atoms in the alkoxyalkyl radical and up to three ether groups per alkoxyalkyl radical, wherein the ratio of isocyanate groups to isocyanate-reactive groups is 0.5:1 to 2.0:1, wherein the composition is characterized in that the polyisocyanate of the polyisocyanate component A) is produced by gas-phase phosgenation of araliphatic polyamines, in particular of 1,3-xylylenediamine and/or 1,4-xylylenediamine.

The present invention further provides a process for producing transparent polythiourethane articles by reaction of a composition containing or consisting of A) a polyisocyanate component containing at least one polyisocyanate having a functionality of isocyanate groups of at least 2 per molecule, B) a thiol component containing or consisting of at least one polythiol having a functionality of thiol groups of at least 2 per molecule
and optionally
C) auxiliary and additive agents,
wherein the ratio of isocyanate groups to isocyanate-reactive groups is 0.5:1 to 2.0:1,
wherein the polyisocyanate of the polyisocyanate component A) is produced by gas-phase phosgenation of aliphatic, cycloaliphatic, aromatic or araliphatic polyamines.

The preferred embodiments and definitions set out above apply analogously to the compositions employed in the process according to the invention.

The process may in particular be performed without solvent addition, i.e. in solvent-free fashion, and the nitrile addition is not to be understood as solvent addition in this context.

Irrespective of the type of chosen starting substances in the process according to the invention the reaction of the polyisocyanate mixtures A) with the thiol component B) and optionally further isocyanate-reactive components is effected adhering to an equivalent ratio of isocyanate groups to isocyanate-reactive groups of 0.5:1 to 2.0:1, preferably of 0.7:1 to 1.3:1, more preferably of 0.8:1 to 1.2:1.

In the process according to the invention the components of the composition according to the invention are preferably mixed, optionally in solvent-free form, in the above-stated equivalent ratio of isocyanate groups to isocyanate-reactive groups using suitable mixing apparatuses and charged into open or closed molds by any desired method, for example by simple hand-pouring but preferably using suitable machines, for example the low-pressure or high-pressure machines customary in polyurethane technology, or by the RIM process. Curing may be performed in a temperature range of 40° C. to 180° C., preferably of 50° C. to 140° C., particularly preferably of 60° C. to 120° C., and optionally under elevated pressure of up to 300 bar, preferably up to 100 bar, particularly preferably up to bar.

The polyisocyanates and optionally also the other starting components may be degassed by application of vacuum.

The molded articles thus produced from the according to the invention can generally be demolded after a short time, for example after 2 to 60 min. A post-curing at a temperature of 50° C. to 100° C., preferably at 60° C. to 90° C., may optionally follow.

Compact light- and weather-resistant polythiourethane articles having high resistance toward solvents and chemicals and outstanding mechanical properties, in particular an excellent heat resistance even at higher temperatures of for example 80° C., are obtained in this way. Compared to the prior art systems which were produced using diisocyanates manufactured by liquid-phase phosgenation the molded articles according to the invention feature a higher transparency and a lower propensity for formation of cloudiness.

The present invention further provides a compact transparent polythiourethane article obtainable by reaction of the components of the composition according to the invention. This polythiourethane article may be a glass-replacement part, an optical, optoelectronic or electronic component part, an optical lens or a spectacle glass. Specific applications are for example production of/use as glass-replacement panes, for example sunroofs, front, rear or side panes in automotive or aeronautical production, as safety glass, solar modules, light emitting diodes, lenses or collimators, as are employed for example as auxiliary optics in LED lamps or automotive headlamps.

The present invention further relates to the use of polyisocyanates which are produced by gas-phase phosgenation of aliphatic, cycloaliphatic, aromatic or araliphatic polyamines for producing transparent polythiourethane articles.

However, a particularly preferred field of application for the molded polythiourethane articles according to the invention obtainable from the compositions according to the invention is the production of lightweight plastic spectacle glasses having a high refractive index and a high Abbe number. Spectacle glasses produced according to the invention feature outstanding mechanical properties, in particular hardness and impact resistance and also good scratch resistance and are moreover easy to process and colorable as desired.

The invention will now be more particularly discussed with reference to exemplary embodiments and a FIGURE.

EXAMPLES

FIG. 1 depicts a schematic diagram of a suitable plant for gas-phase phosgenation. This plant is particularly suitable for manufacturing 1,3-XDI and 1,4-XDI with contents of nitriles >0.1 wt % based on the manufactured isocyanate.

All percentages are based on weight, unless stated otherwise.

Measurement of the refractive indices and Abbe numbers was effected using an A. KRÜSS Optronic GmbH Model AR4D Abbe refractometer at 23° C. as per DIN EN ISO 489:1999-08.

Transmission and haze measurements as per ASTM D 1003 were performed with a Byk Haze-Gard Plus using standard light type D65 (defined in DIN 6173).

The chemicals used were employed without further pretreatment:

Tinuvin® 571: alkylphenol-substituted benzotriazole (BASF)

Zelec UN: mixture of long-chain mono- and dialkyl phosphate (Steppan)

DBC: dibutyltin dichloride (Acros Organics)

DMPT: 4-mercaptomethyl-1,8-dimercapto-3,6-dithiaoctane (Bruno Bock GmbH)

Performing the Phosgenation of 1,3-XDA

Example 1

In a plant for gas-phase phosgenation comprising an amine evaporation stage as per FIG. 1, a tubular reactor (L: 9350 mm, internal diameter 134.5 mm) having a coaxial nozzle arranged along the reactor axis (internal diameter 134.5 mm) and a downstream isocyanate condensation stage, 200 kg/h of 1,3-XDA were continuously evaporated at a pressure of 650 mbar abs. with introduction of a nitrogen stream of 10 kg/h, the temperature in the pumped circulation circuit (3200 kg/h) being kept at 150° C. by cooling in a heat exchanger (WT). 500 ppm Tinuvin® 571 had previously been added to the pumped circulation circuit. The supply temperature to the evaporator (V) was 255° C., the entry temperature of the cooling medium into the heat exchanger (WT) was 40° C. and the average residence time of the 1,3-XDA in the pumped circulation circuit was 35 minutes. After exiting the evaporator the stream composed of gaseous 1,3-XDA and nitrogen was heated to 280° C. in a further heat exchanger and supplied to the reactor via the coaxial nozzle. Simultaneously and in parallel thereto, 750 kg/h of phosgene were heated to 310° C. and on the annular space left free by the nozzle likewise continuously supplied to the reactor in which the two reactant streams were mixed and brought to reaction. The velocity of the gas stream in the reactor was about 20 m/s and the velocity ratio of the amine/nitrogen stream to the phosgene stream was 8.8. The pressure at the vacuum pump was 600 mbar abs.

After an average residence time in the reactor of 0.48 seconds the gas stream containing the reaction product 1,3-XDI was cooled by injection cooling with monochlorobenzene and condensed, the temperature of the liquid phase in the quench being about 90° C. The content of 3-chloromethylbenzyl isocyanate determined by gas chromatography was 0.4% based on the sum of 1,3-XDI and 3-Cl-XI. The reaction mixture was then freed of HCl and phosgene and worked up by distillation. The yield of 1,3-XDI was 95% of theory.

Example 2

In the abovedescribed plant 160 kg/h of 1,3-XDA were analogously evaporated at a pressure of 500 mbar abs. with introduction of a nitrogen stream of 4 kg/h, the temperature in the pumped circulation circuit (3200 kg/h) being kept at 150° C. by cooling in a heat exchanger (WT). 500 ppm Tinuvin® 571 had previously been added to the pumped circulation circuit. The supply temperature to the evaporator (V) was 240° C., the entry temperature of the cooling medium into the heat exchanger (WT) was 40° C. and the average residence time of the 1,3-XDA in the pumped circulation circuit was 43 minutes. The stream composed of gaseous 1,3-XDA and nitrogen was heated to 280° C. in a further heat exchanger and supplied to the reactor via the coaxial nozzle. Simultaneously and in parallel thereto, 500 kg/h of phosgene were heated to 310° C. and on the annular space left free by the nozzle likewise continuously supplied to the reactor in which the two reactant streams were mixed and brought to reaction. The velocity of the gas stream in the reactor was about 20 m/s and the velocity ratio of the amine stream to the phosgene stream was 8.8. After an average residence time in the reactor of 0.46 seconds the gas stream containing the reaction product 1,3-XDI was cooled by injection cooling with monochlorobenzene and condensed, the temperature of the liquid phase in the quench being about 90° C.

The content of 3-chlormethylbenzyl isocyanate determined by gas chromatography was 0.3% based on the sum of 1,3-XDI and 1.3-Cl-XI. The reaction mixture was then freed of HCl and phosgene and worked up by distillation. The yield of 1,3-XDI was 92% of theory.

Production of XDI Manufactured by Liquid-Phase Phosgenation for Comparison

Example 3 (Comparative)

With stirring and cooling a solution of 5 parts by weight of 1,3-XDA in 50 parts by weight of monochlorobenzene was metered into a solution of 20 parts by weight of phosgene in 25 parts by weight of monochlorobenzene at 0-10° C. and on completion of the addition the mixture was allowed to reach room temperature. The temperature was subsequently increased to reflux with introduction of phosgene according to gas evolution and phosgenation was continued until the solution eventually became clear. Once the clear point had been reached (about 4-5 h) phosgenation was continued for a further 30 minutes. Phosgene introduction was then terminated and the mixture was refluxed with introduction of nitrogen until phosgene was no longer detectable in the offgas.

The reaction mixture was then worked up by distillation to obtain XDI as a colorless liquid having a boiling point of 130° C./0.2 mbar. The yield of 1,3-XDI was 80% of theory.

Example 4

2 kg of the XDI obtained in example 2 were fractionally distilled through a column. The first 500 g were discarded as forerun and 1 kg of colorless 1,3-XDI was obtained as the main fraction. This main fraction was admixed with 1.4 g of Zelec UN (Steppan) at room temperature and left to stand for 24 h. The HC content of the sample after distillation, measured as per ASTM specification D4663-98, was 105 ppm.

The content of 3-isocyanatomethylbenzonitrile was determined by dissolving 1 g of 1,3-XDI in 100 ml of acetonitrile. 100 µl of this solution were mixed with 900 µl of a diethylamine solution (0.2 g of diethylamine in 100 ml of acetonitrile) and stored at 65° C. for 30 minutes prior to HPLC-MS measurement. Purity was determined by integration of the areas of the signals in the UV. It was assumed that all compounds show the same UV absorption and that no compounds without a UV absorption are present in the samples. A further assumption was that no degradation reactions take place during measurement. The following program was chosen for HPLC-MS measurement:

Synapt G2-S HR-MS, ACQUITY UPLC (Waters) QS. No.: 02634
UV: PDA (Total Absorbance Chromatogram)
Column: Kinetex 100×2.1 mm_1.7 µm
Column temperature: 30° C.
The mobile phase consisted of:
Solvent: A) water+0.05% formic acid
B) acetonitrile+0.05% formic acid
Flow rate: 0.5 ml/min
Gradient: t0/5% B_t0.5/5% B_t6/100% B_t7/100% B_t7.1/5% B_t8/5% B The sample was found to contain 98.4% 1,3-XDI and 0.7% 3-isocyanatomethylbenzonitrile.

Example 5

2 kg of the XDI obtained in example 3 were fractionally distilled through a column. The first 800 g were discarded as forerun and 700 g of colorless 1,3-XDI were obtained as the main fraction. This main fraction was admixed with 0.98 g of Zelec UN at room temperature and left to stand for 24 h. The HC content of the sample after distillation measured as per ASTM specification D4663-98 was 108 ppm.

Analogously to example 4, purity determination by HPLC was performed. No 3-isocyanatomethylbenzonitrile was found in the course of this. The proportion of 1,3-XDI was 95.4%.

Production of Polythiourethane Spectacle Glasses

Example 6

A casting mold was first prepared by clamping together two glass shell molds (85 mm diameter, internal radius 88 mm, Shamir Insight, Inc., IL) with a gap of 8 mm and a plastic sealing ring to form a casting cavity. The mold gap is 8 mm at each point of the lens.

The casting system was produced as follows:
In a flask, 0.002 g of dibutyltin dichloride (DBC) were dissolved in 94.59 g of 1,3-XDI from example 4 and the mixture was evacuated at 10 mbar for 30 minutes. 90.00 g of DMPT (4-mercaptomethyl-1,8-dimercapto-3,6-dithiaoctane) were then added into the flask and the final mixture was stirred and degassed at 10 mbar for 30 minutes. This mixture was then filtered through a 5 μm filter, drawn into a syringe and the casting mold was completely filled therewith.

The filled casting mold was cured in a drying cabinet with the temperature profile: 15 hours at 65° C.; 2 hours at 100° C. and a further 2 hours at 120° C. The casting mold was then cooled to room temperature and, after complete cooling, first the sleeve and then the two glass articles were manually removed.

A spectacle glass blank that was completely clear, transparent and free from cloudiness was obtained in this way.

Transmission was 90.3% for standard light type D65, haze was 2.1. The refractive index nE was 1.67 at 23° C.

Example 7

Analogously to example 6 a spectacle glass blank was produced using 1,3-XDI from example 5. This spectacle glass blank was completely cloudy, transmission was only 29.7%, haze was 100.

The invention claimed is:

1. A composition for producing transparent polythiourethane articles comprising
    A) a polyisocyanate component containing at least one polyisocyanate having a functionality of isocyanate groups of at least 2 per molecule,
    B) a thiol component containing at least one polythiol having a functionality of thiol groups of at least 2 per molecule,
    wherein the ratio of isocyanate groups to isocyanate-reactive groups is 0.5:1 to 2.0:1,
    wherein
    the composition further contains
    C) at least one aromatic nitrile.

2. The composition as claimed in claim 1, wherein the composition contains 0.0025 to 10 wt % based on the entire composition of aromatic nitrile.

3. The composition as claimed in claim 1, wherein the at least one aromatic nitrile comprises an isocyanate group.

4. The composition as claimed in claim 1, wherein the nitrile is selected from the group consisting of benzonitrile, 3-(isocyanatomethyl)benzonitrile, 4-(isocyanatomethyl)benzonitrile, 3-(chloromethyl)benzonitrile, 4-(chloromethyl)benzonitrile and mixtures thereof.

5. The composition as claimed in claim 1, wherein the polyisocyanate is selected from the group consisting of 1,3-bis(isocyanatomethyl)benzene (1,3-XDI), 1,4-bis(isocyanatomethyl)benzene (1,4-XDI), 2,5-bis(isocyanatomethyl)bicyclo[2.2.1]heptane, 2,6-bis(isocyanatomethyl)bicyclo[2.2.1]heptane, 1,4-bis(isocyanatomethyl)cyclohexane, 1,3-bis(isocyanatomethyl)cyclohexane, 2,2'-diisocyanatodicyclohexylmethane, 2,4'-diisocyanatodicyclohexylmethane, 4,4'-diisocyanatodicyclohexylmethane (H12-MDI), 1-isocyanato-3,3,5-trimethyl-5-isocyanatomethylcyclohexane (isophorone diisocyanate; IPDI) and mixtures thereof.

6. The composition as claimed in claim 1, wherein the polyisocyanate is an aromatic polyisocyanate and the nitrile is derived from the same polyamine as the polyisocyanate.

7. The composition as claimed in claim 5, wherein the polyisocyanate is selected from 1,3-bis(isocyanatomethyl)benzene (1,3-XDI) and the nitrile from 3-(isocyanatomethyl)benzonitrile and/or the polyisocyanate is selected from 1,4-bis(isocyanatomethyl)benzene (1,4-XDI) and the nitrile from 4-(isocyanatomethyl)benzonitrile.

8. The composition as claimed in claim 1, wherein the polythiol is selected from group consisting of 4-mercaptomethyl-1,8-dimercapto-3,6-dithiaoctane, 2,5-bismercaptomethyl-1,4-dithiane, 1,1,3,3-tetrakis(mercaptomethylthio)propane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, trimethylolpropane tris(3-mercaptopropionate), trimethylolethane tris(2-mercaptoacetate), pentaerythritol tetrakis(2-mercaptoacetate), pentaerythritol tetrakis(3-mercaptopropionate) and mixtures thereof.

9. The composition as claimed in claim 1, wherein component C) is one or more of a catalyst, a surface-active agent, a UV stabilizer, an antioxidant, a fragrance, a mold release agent, a filler or a pigments.

10. The composition as claimed in claim 9, wherein the mold release agent is a phosphate ester.

11. The composition as claimed in claim 9, wherein the mold release agent is mono- and/or dialkoxyalkyl phosphates having 2 to 12 carbon atoms in the alkoxyalkyl radical and up to three ether groups per alkoxyalkyl radical.

12. A process for producing a transparent polythiourethane article comprising reacting a composition comprising
    A) a polyisocyanate component containing at least one polyisocyanate having a functionality of isocyanate groups of at least 2 per molecule,
    B) a thiol component containing at least one polythiol having a functionality of thiol groups of at least 2 per molecule,
    wherein the ratio of isocyanate groups to isocyanate-reactive groups is 0.5:1 to 2.0:1,
    wherein
    the composition further contains
    C) at least one aromatic nitrile.

13. A transparent polythiourethane article obtained by reaction of the components of a composition as claimed in claim 1, wherein the article is selected from the group consisting of a glass-replacement part, an optical, optoelectronic or electronic component part, an optical lens and a spectacle glass.

* * * * *